United States Patent
Buchdunger et al.

(10) Patent No.: US 8,124,611 B2
(45) Date of Patent: *Feb. 28, 2012

(54) INHIBITORS OF THE MUTANT FORM OF KIT

(75) Inventors: Elisabeth Buchdunger, Neuenburg (DE); Doriano Fabbro, Arlesheim (CH)

(73) Assignee: Novartis AG, Basel (CH)

( * ) Notice: Subject to any disclaimer, the term of this patent is extended or adjusted under 35 U.S.C. 154(b) by 65 days.

This patent is subject to a terminal disclaimer.

(21) Appl. No.: 12/700,106

(22) Filed: Feb. 4, 2010

(65) Prior Publication Data

US 2010/0179179 A1  Jul. 15, 2010

Related U.S. Application Data

(62) Division of application No. 10/579,586, filed as application No. PCT/EP2004/013045 on Nov. 17, 2004.

(60) Provisional application No. 60/520,714, filed on Nov. 18, 2003.

(51) Int. Cl.
   *A61K 31/506* (2006.01)
   *C07D 401/14* (2006.01)
   *C07D 213/38* (2006.01)

(52) U.S. Cl. ........................ 514/275; 544/331

(58) Field of Classification Search ............... None
   See application file for complete search history.

(56) References Cited

U.S. PATENT DOCUMENTS

| | | | |
|---|---|---|---|
| 5,521,184 | A | 5/1996 | Zimmermann |
| 5,543,520 | A | 8/1996 | Zimmermann |
| 6,107,301 | A | 8/2000 | Aldrich et al. |
| 7,169,791 | B2 | 1/2007 | Breitenstein et al. |
| 2004/0157855 | A1 | 8/2004 | Heinrich et al. |
| 2005/0054617 | A1 | 3/2005 | Moussy et al. |
| 2005/0095237 | A1 | 5/2005 | Emtage |
| 2007/0299049 | A1 | 12/2007 | Coutre |
| 2008/0176879 | A1 | 7/2008 | Alland et al. |
| 2010/0210673 | A1 | 8/2010 | Alland et al. |

FOREIGN PATENT DOCUMENTS

| | | |
|---|---|---|
| AU | 2004290902 | 11/2001 |
| EP | 0564409 | 2/2010 |
| WO | 95/09847 | 4/1995 |
| WO | 95/09852 | 4/1995 |
| WO | 97/19065 | 5/1997 |
| WO | WO 98/35958 | 8/1998 |
| WO | 98/55152 | 12/1998 |
| WO | 99/03854 | 1/1999 |
| WO | 99/25372 | 5/1999 |
| WO | WO 03/007924 A2 | 1/2003 |
| WO | 03/076660 | 9/2003 |
| WO | 2004/005281 | 1/2004 |
| WO | 2004/032935 | 4/2004 |
| WO | 2005/049032 | 6/2005 |

OTHER PUBLICATIONS

U.S. Appl. No. 10/579,586, filed Jan. 17, 2007.*
U.S. Appl. No. 11/996,081, filed Jan. 18, 2008.*
Armstrong et al., "Inhibition of FLT3 in MLL: Validation of a therapeutic target identified by gene expression based classification in Cancer Cell.", vol. 3, pp. 173-183, (Feb. 2003).
Antoriescue et al., "Association of KIT Exon 9Mutations with Nongastric Primary Site and Aggressive Behavior.", Clinical Cancer research, vol. 9, pp. 3329-3337, (Aug. 15, 2003).
Looijenga et al.,"Stem Cell Factor Receptor (c-KIT) Codon 816 Mutations Predict Development of Bilateral Testicular Germ-Cell Tumors", Cancer Research, No. 63, pp. 7674-7678, (Nov. 15, 2003).
Algros MP et al., "Small intestinal stromal tumors with skenoid fibers, Clinicopathological study of three cases,", Ann Chir.,vol. 128(6), pp. 397-401 (2003). abstract, on-line [found in the internet under www.pubmed.com 08.07.2008], PMID; 12943839 [PubMed—indexed for Medline].
Cecil Textbook of Medicine, edited by Bennet, J.C., and Plum F., $20^{th}$ edition, vol. 1, pp. 1004-1010, 1996.
Heinrich et al., "Inhibition of KIT Tyrosine Kinase Activity: A Novel Molecular Approach to the Treatment of KIT—Positive Malignancies", Journal of Clinical Oncology, vol. 20, No. 6, pp. 1692-1703 Mar. 15, 2002.
Ning et al: "Activating mutations of c-kit at codon 816 confer drug resistance in human leukemia cells", Leukemia and Lymphoma, vol. 41(5-6), pp. 513-522, May 2001.
Gotlib et al., "PKC412, inhibitor of the KIT tyrosine kinase, demonstrates efficacy in mast cell leukemia with the D816V kIT mutation," Blood, vol. 102(11), p. 919A (2003).
Stone et al., "PKC412, an oral FLT3 inhibitor, has activity in mutant FLT3 acute myeloid leukemia (AML): A phase II clinical trial ," Blood, vol. 100(11), abstract No. 316 (2002).
Wang et al., "Pharmacokinetics and pharmacodynamics of PKC412, a FLT3 receptor inhibitor, following oral doses in acute myeloid leukemia (AML) patients," Blood, vol. 102(11) (2003).
Weisberg et al., "Inhibition of mutant FLT3 receptors in leukemia cells by the small molecule tyrosine kinase inhibitor PKC42," Cancer Cell, vol. 1(5), pp. 433-443 (2002).
Knapper et al., "The in vito sensitivity of primary AML blasts to two flt3 inhibitors and cytarabine appears independent of flt3 mutation status," Blood, vol. 102(11), p. 24a (2003).

(Continued)

Primary Examiner — David Romeo
(74) Attorney, Agent, or Firm — Stephen E. Johnson

(57) ABSTRACT

The present invention relates to the treatment of KIT dependent diseases that are characterized by a mutant form of KIT whereby the mutant KIT is identified and an appropriate inhibitor of the mutant KIT is administered.

2 Claims, 1 Drawing Sheet

OTHER PUBLICATIONS

Estey Elihu et al., "A randomized phase II trial of the tyrosine kinase inhibitor PKC412 in patients (pts) with acute myeloid leukemia (AML)/high-risk myelodysplastic syndromes (MDS) characterized by wild-type (WT) or mutated FLT3," Blood, vol. 102(11) pp. 614a-615a (2003).

Giles F. J., "New drugs in acute myeloid leukemia," Current Oncology Reports, Current Science. GB, vol. 4(5), pp. 369-374 (2002).

Rodoz et al., "Phase I trial of PTK787/ZK 222584, an inhibitor of vascular endothelial growth factor receptor tyrosine kinases, in acute myeloid leukemia and myelodysplastic syndrome," Blood, vol. 100 (11), Abstract No. 1308 (2002).

De Bont et al., "Decreased in-vitro cellular drug resistance by addition of vascular endothelial growth factor receptor (VEGFR) inhibitor, PTK787/ZK 222584, to conventional chemotherapy in pediatric AML." Leukemia, vol. 17(3), p. 668 (2003).

Tefferi A et al: "Imatinib therarpy in clonal eosinophilic disorders, including systemic mastocytosis", International Journal of Hematology, vol. 49:441-447, 2004.

Valent P et al: "Mastocytosis: pathology, genetics and current options for therapy", Leuk Lymphoma, Jan. 2005, vol. 46(1), pp. 35-48.

Pullarkat VA et al: "Systemic mastocytosis with associated clonal hematological non-mast-cell lineage disease: analysis of clinicopathologic features and activating c-kit mutations", American Journal Hematol. May 2003, vol. 73(1). pp. 12-17.

Horny HP et al: "Systemic mastocytosis with associated clonal hematological non-mast cell lineage diseases, a histophathological challenge", Jun. 2004. vol. 57(6), pp. 604-608.

Lim Ken-Hong et al: "Systemic mastocytosis in 342 consecutive adults: survival studies and prognostic factors", Blood, Jun. 4, 2009, vol. 113, No. 23, pp. 5727-5736.

Giles, F et al, "A Phase 1/11 Study of AMN107. a Novel Aminopyrimidine Inhibitor of Bcr-Abl, on a Continuous Daily dosing Schedule in Adult Patients (pts) with Imatinib-resistant Advanced Phase Chronic Myeloid Leukemia (CML) or Relapsed/Refractory Philadelphia Chromosome (Ph+) Acute Llymphocytic Leudemia (ALL).", Blood, (ASH Annual Meeting Abstracts), vol. 104,Abstract 22, (2004).

Zermati. Y et al. "Effects of the tyrosine kinase inhibitor STI 571 on the kinase activity of wild type and various mutated c-kit receptors found in mast cell neoplasms," Publ. ASH (2000).

Heinrich C et al. "Inhibition of c-kit receptor tyrosine kinase activity by STI 571, a selective tyrosine kinase inhibitor." , Blood, vol. 96, No. 3, pp. 925-931 (2000).

Akin C et al. ,Effects of the tyrosine-kinase inhibitor STI571 on mutated kit and neoplastic mast cells, Blood, vol. 96 (11), pp. 747a, Abstract #3231 (2000).

Wedemeyer J et al. "Roles of mast cells and basophils in innate and acquired immunity", Current Opinion in Immunology, vol. 12 (6), pp. 624-631 (2000).

Secor V H et al. "Mast cells are essential for early onset and severe disease in a murine model of multiple sclerosis", The Journal of Experimental Medicine, vol. 191, No. 5, pp. 813-821 (2000).

Berlin A A et al. "Treatment of cockroach allergen asthma model with Imatinib Attenuates Airway Responses,", Am. J. Respir. Crit. Care Med., vol. 171, pp. 35-39 (2005).

London C A et al. "Spontaneous canine roast cell tumors express tandem duplications in the proto-oncogene c-kit.", Experimental Hematology 27, pp. 687-697 (1999).

Ma Y et al. "Clustering of activating mutations in c-KIT's Juxtamembrane coding region in Canine Mast Cell Neoplasms", J. Invest. Dermatol. 112, pp. 165-170 (1999).

Ma Y et al. Indolinone derivatives inhibit constitutively activated KIT Mutants and Kill Neoplastic Mast Cells, J. Invest. Dermatol. 114, pp. 392-394 (2000).

Longley B J et al. "Classes of c-KIT activating mutations: proposed mechanisms of action and implications for disease classification and therapy", Leukemia Research 25, pp. 571-576 (2001).

Longley B J et al. "Activating and dominant inactivating c-KIT catalytic domain mutations in distinct clinical forms of human mastocytosis", Proc Natl. Acad. Sci. USA, vol. 96, pp. 1609-1614 (1999).

Beghini, A et al., "c-kit Activating Mutations and Mast Cell Proliferation in Human Leukemia", Correspondence, pp. 701-702, Jul. 15, 1998.

Akin C et al., "Soluble stem cell factor receptor (CD117) and IL-2 receptor alpha chain (CD25) levels in the plasma of patients with mastocytosis: relationships to disease severity and bone marrow pathology.", Blood, vol. 995, No. 4, pp. 1267-1273 (2000).

Ma Y et al., "The c-KIT mutation causing human mastocytosis is resistant to STI571 and other KIT kinase inhibitors; kinases with enzymatic site mutations show different inhibitor sensitivity profiles than wild-type kinases and those with regulatory-type mutations.", Blood, vol. 99, No. 5, pp. 1741-1744 (2002).

Heinrich M C et al. "Inhibition of KIT Tyrosine Kinase Activity: A Novel Molecular approach to the Treatment of KIT-Positive Malignancies", Journal of Clinical Oncology, vol. 20, No. 6, pp. 1692-1703 (2002).

Takeuchi K et al. "STI571 inhibits growth and adhesion of human mast cells in culture", Journal of Leukocyte Biology, vol. 74, pp. 1026-1034 (2003).

Weisberg et al., "Characterization of AMN 107, a selective inhibitor of native and mutant Bcr-Abl," Cancer Cell. vol. 7, No. 2, pp. 129-141 (2005).

Giles et al., "A Phase IIII study of AMN107, a novel aminopyrimidine inhibitor of bcr-abl, on a continous daily dosing schedule in adult patients (pts) with imatinib-resistant advanced phase chronic myeloid leukemia (CML) or relapsed/refractory Philadelphia chromosome (Ph plus) acute lymphocytic leukemia (ALL)." Blood, vol. 104, No. 11, Part 1, pp. 10A-11A (2004).

Pardanani et al., "CHIC2 deletion, a surrogate for FIP1L1-PDGFRA fusion, occurs in mastocytosis associated with eosinophilia and predicts response to imatinib mesylate therapy," Blood, vol. 102, No. 9, pp. 3093-3096 (2003).

Merck Manual about Mastocytosis, 2008.

Cross NCP, et al: "Tyrosine kinase fusion genes in chronic myeloroliferative dieseases", Leukemia (2002) vol. 16, pp. 1207-1212, 2002.

Piccaluga PP, et al: "Imatinib mesylate in the treatment of hematologic malignancies", Expert Opinion in Biological Therapy, 7(10), pp. 1517-1611, 2007.

Bold Guido, et al: "New Anilinophthalazines as potent and orally well absorbed inhibitors of the VEGF receptor tyrosine kinases useful as antagonists of tumor-driven angiogenesis", Journal of Medicinal Chemistry, vol. 43, No. 12, pp. 2310-2323, May 27, 2000.

Sakuma Yuji, et al.: "Alterations of the c-kit gene in testicular germ cell tumors", Cancer Science, vol. 94, No. 6, Jun. 2003, pp. 486-491.

Cools Jan, et al: "PKC412 overcomes resistance to imatinib in a murine model of FIP1L1-PDGFRα-induced myeloproliferative disease", Cancer Cell, vol. 3, No. 5 pp. 459-469. May 2003.

Testa Ugo: "Kit mutations in cancer and their treatment with protein kinase inhibitors", Drugs of the Future 2008, vol. 33(2), pp. 161-174 2008.

Roberts Kathryn G., et al: "Resistance to c-kit kinase inhibitors conferred by V654A mutation", Mol Cancer Therapy 2007, vol. 6(3), pp. 1159-1165, Mar. 2007.

Lacal Juan Carlos: "Changing the course of oncogenesis: the development of tyrosine kinase inhibitors", EJC Supplements 4, pp. 14-20 2006.

Freshney R. Ian: "Culture of animal cells, a manual of basic technique", Alan R. Liss, Inc. 1983, New York, pp. 2-4.

Dermer Gerald B.: Another anniversary for the war on cancer, Bio/technology vo. 12, pp. 320, Mar. 12, 1994.

MSNBC News Services: "Mixed results on cancer drug", Nov. 9, 2000.

Gura: Systems for identifying new drugs are often faulty, Science, vol. 278, pp. 1041-1042, Nov. 7, 1997.

* cited by examiner

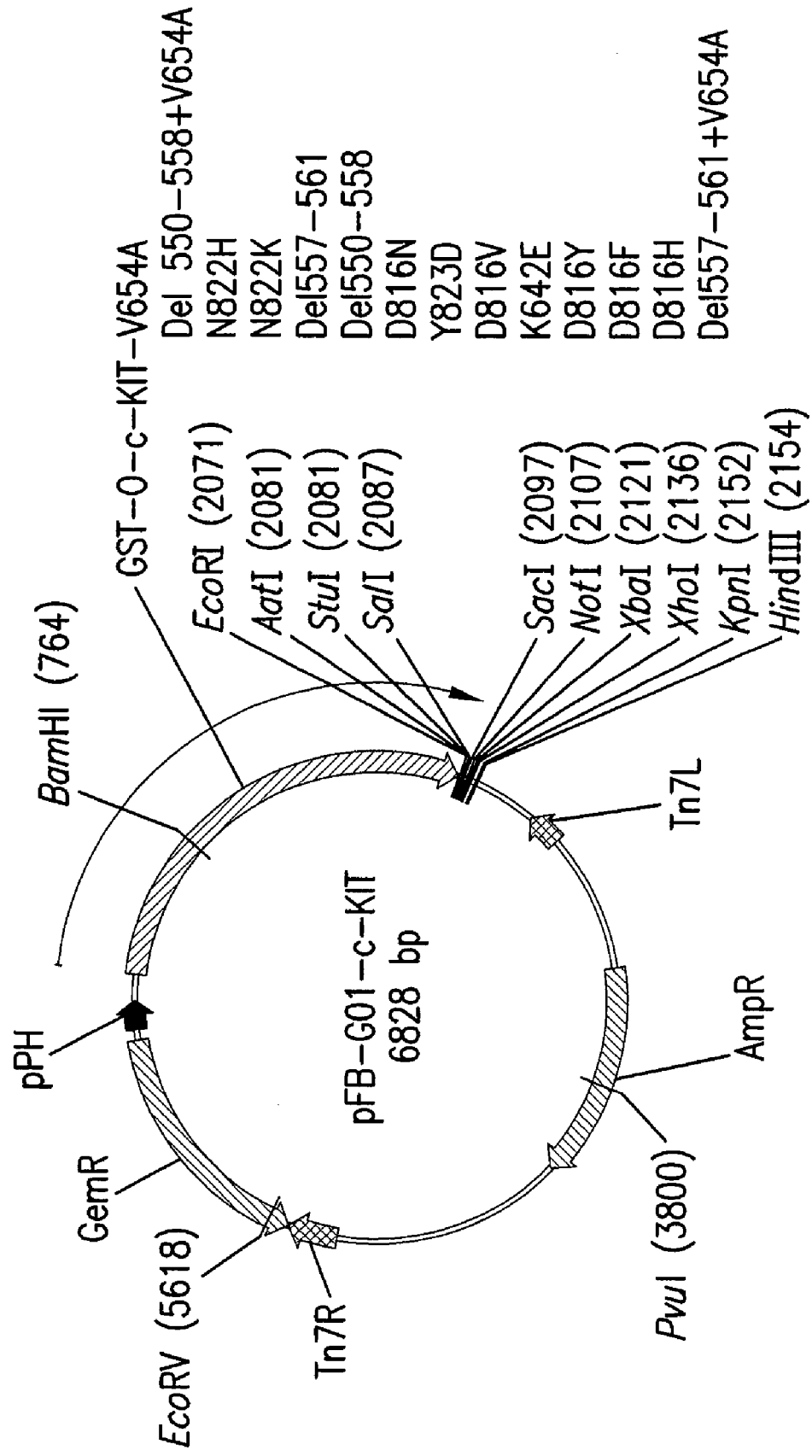

INHIBITORS OF THE MUTANT FORM OF KIT

This application is a divisional of application Ser. No. 10/579,586 filed Jan. 17, 2007, which is National Stage of International Application No PCT/EP2004/013045 filed on Nov. 17, 2004, which claims benefit of U.S. Provisional Application No. 60/520,714 filed Nov. 18, 2003, which in their entirety are herein incorporated by reference.

The present invention relates to the treatment of KIT dependent diseases that are characterized by a mutant form of KIT whereby the mutant KIT is identified and an appropriate inhibitor of the mutant KIT is administered.

The c-kit gene encodes a receptor protein tyrosine kinase, which is herein referred to as KIT, but which is also known as mast/stem cell growth factor receptor. The amino acid sequence of KIT and the nucleotide sequence of the c-kit gene are known. See Swiss Prot.: P10721. Upon binding its ligand, stem cell factor, KIT forms a dimer that is autophosphorylated and activates signaling cascades that lead to cell growth. Mutations that lead to an activated form of KIT, especially forms that are activated independently of its ligand, are known and are believed to play a role in certain proliferative diseases, such as mast cell diseases, like mastocytosis, particularly systemic mastocytosis, acute myelogenous leukemia, gastrointestinal stromal tumors, sinonasal NK/T-cell lymphoma, seminomas and dysgerminomas.

Imatinib, which is marketed as its mesylate salt under the brandname GLIVEC or GLEEVEC, is known to inhibit wild type KIT and certain KIT mutations e.g. those in exons commonly found in gastrointestinal stromal tumors (GIST). However, it is also inactive or significantly less active against certain other mutant forms of KIT, for example the D816V mutation commonly found in systemic mastocytosis. The present invention is based upon research that correlates the treatment of a disease characterized by a mutant form of KIT with an appropriate alternative pharmaceutical therapy based on the alternative's ability to inhibit the mutant KIT.

Thus, the present invention relates to a method of treating a KIT dependent disease in a patient, which comprises
  (a) identifying the mutant form of KIT associated with the KIT dependent disease; and
  (b) administering to the patient an effective mutant KIT-inhibiting amount of an inhibitor selected from the group consisting of midostaurin, vatanalib and compound A.

KIT dependent diseases are generally proliferative diseases that are characterized by excessive KIT kinase activity due to an activating mutation in KIT. Such activating mutations are known in the art and are identified by techniques known in the art.

KIT dependent diseases include diseases characterized by the following known KIT mutations: D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C and T670I.

In an important embodiment of the present invention, the KIT dependent disease is resistant to treatment with imatinib. A KIT dependent disease that is resistant to imatinib is generally a KIT dependent disease as described above wherein imatinib, administered at a dose of 400-1000 mg/day, does not provide sufficient inhibition of the mutant KIT to effect a significant therapeutic benefit. Generally, mutant KIT that is resistant to imatinib has an in vitro $IC_{50}$ of the mutant KIT greater than about 3 micromolar. Imatinib resistant KIT mutations include D816F, D816H, D816N, D816Y, D816V, T670I and mutant forms that include V654A.

The selection of a compound that inhibits the mutant form of KIT is based on testing the compound or a number of compounds for their ability to inhibit the mutant KIT. Such testing is carried out by standard inhibition assays that are known in the art or within the skill of the artisan.

The KIT inhibitors utilized in accordance with the present method include midostaurin, vatalanib and compound A. Midostaurin (U.S. Pat. No. 5,093,330) and vatalanib (WO 98/35958) are known in the art. Compound A is a compound of the formula

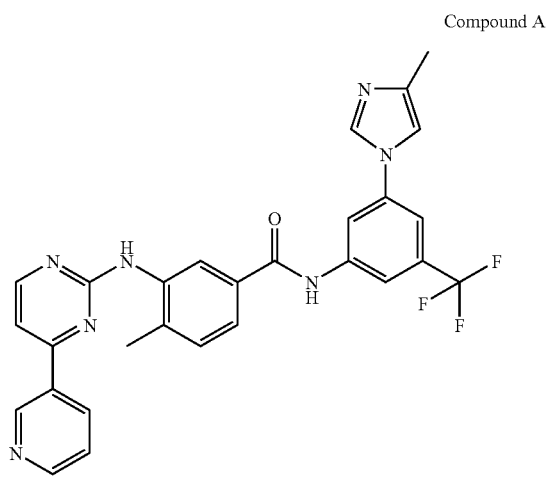

Compound A

And may be produced according to WO 04/005281.

Appropriate dosages of midostaurin, vatanalib and compound A are determined by routine methods.

An appropriate dose of midostaurin is administered, e.g., once, twice or three times a day, for a total dose of 25-300 preferably 50-300 more preferably 50-100 most preferably 100-300 mg daily, e.g., two or three times a day, for a total dose of 150-250 mg, preferably 225 mg daily.

An appropriate daily dose of vatanalib is an amount in the range from 300-4000 mg, e.g., in the range from 300-2000 mg/day or 300-1500 mg/day, in particular, 300, 500, 750, 1000, 1250, 1500 or 2000 mg/day, particularly 1250 mg/day.

The daily dose of compound A for a 70 kg/person is from approximately 0.05-5 g, preferably from approximately 0.25-1.5 g.

BRIEF DESCRIPTION OF THE DRAWINGS

FIG. 1 illustrates mutant insertion points in the Bac-to-Bac donor vector pFB-GST-01.

EXAMPLES

The human KIT gene encoding aa 544-976 was cloned into the baculovirus donor plasmid pFB-GST-01. This coding sequence was excised using restriction endonucleases Bam H1 and EcoR1 and ligated to a Bac-to-Bac donor vector pFB-GEX-P1 with compatible ends. Subsequently the desired mutations were brought into the KIT gene by methods know to a person skilled in the art. Due to a frame shift within the original plasmid that was used to generate the mutant coding sequences, the mutated plasmid inserts were excised and inserted into the Bac-to-Bac donor vector pFB-GST-01 using the restriction enzymes BamH1-EcoR1 for each mutant shown in FIG. 1. Automated sequencing confirmed the correct sequence to be present for each mutant plasmid.

Bacmid DNA was generated from 10 colonies each of DH10Bac cells transformed with pFB-G01-KIT-mutant plasmid clones as described in materials and methods and these transfected into Sf9 cells. The transfected cells were pelleted and the resultant recombinant baculovirus present in the supernatant medium amplified. Western blotting was applied to the lysed cell pellets to confirm the expression of the GST-c-KIT fusion protein by the viral clones using anti-KIT and anti-GST antibodies for immunodetection.

| Kit Mutation | Vatalanib IC$_{50}$ (μM) (avg) | Compound A IC$_{50}$ (μM) (avg) |
|---|---|---|
| D816F | >10 | >10 |
| D816H | >10 | >10 |
| D816N | >10 | <10 |
| D816Y | >10 | >10 |
| D816V | >10 | >10 |
| K642E | <1 | <10 |
| Y823D | <1 | <1 |
| Del 550-558 | <1 | <2 |
| Del 557-561 | <1 | <2 |
| N822K | <2 | <10 |
| V654A | >10 | >10 |
| N822H | <2 | <10 |
| Del 550-558 + V654A | <10 | <10 |
| Del 557-561 + V654A | >10 | >10 |

| | Midostaurin | | |
|---|---|---|---|
| | average IC50 μM | SEM | N° of values |
| HIS preparation | | | |
| HT-KIT-TA23 wt | 1.7 | 0.15 | 2 |
| HT-KIT TA23-D820G | 0.084 | 0.05 | 2 |
| HT-KIT TA23-T670I | 0.89 | 0.21 | 2 |
| GST preparation | | | |
| GST-KIT wt | 1.8 | 0.26 | 10 |
| GST-KIT Del 557-561 | 0.32 | 0.042 | 3 |
| GST-KIT Del 550-558 | 0.53 | 0.057 | 3 |
| GST-KIT Del 550-558 + V654A | 0.27 | 0.079 | 5 |
| GST-KIT Del 557-561 + V654A | 0.34 | 0.11 | 5 |
| GST-KIT V654A | 0.46 | 0.16 | 5 |
| GST-KIT K642E | 0.64 | 0.036 | 4 |
| GST-KIT R634W | 0.33 | 0.13 | 2 |
| GST-KIT T670I + Del 550-558 | 0.11 | 0.05 | 2 |
| GST-KIT D816F | 0.41 | 0.055 | 5 |
| GST-KIT D816H | 0.35 | 0.078 | 5 |
| GST-KIT D816N | 0.74 | 0.25 | 5 |
| GST-KIT D816Y | 0.29 | 0.11 | 9 |
| GST-KIT D816V | 0.25 | 0.039 | 3 |
| GST-KIT D816H + R634W | 0.08 | 0.04 | 2 |
| GST-KIT N822H | 0.37 | 0.12 | 5 |
| GST-KIT N822K | 0.15 | 0.058 | 5 |
| GST-KIT Y823D | 0.13 | 0.0075 | 3 |

Assay conditions: 1 μM ATP, 5 μg/ml Poly-EY, 10 min incubation at ambient temperature Virus containing media was collected from the transfected cell culture and used for infection to increase its titer. Virus containing media obtained after two rounds of infection was used for large-scale protein expression. For large-scale protein expression 100 cm$^2$ round tissue culture plates were seeded with 5×10$^7$ cells/plate and infected with 1 mL of virus-containing media (approximately 5 MOIs). After 3 days, the cells were scraped off the plate and centrifuged at 500 rpm for 5 minutes. Cell pellets from 10-20, 100 cm$^2$ plates, were re-suspended in 50 mL of ice-cold lysis buffer (25 mM Tris-HCl, pH 7.5, 2 mM EDTA, 1% NP-40, 1 mM DTT, 1 mM PMSF). The cells were stirred on ice for 15 minutes and then centrifuged at 5000 rpm for 20 minutes.

The centrifuged cell lysate was loaded onto a 2 mL glutathione-sepharose column (Pharmacia) and washed 3× with 10 mL of 25 mM Tris-HCl, pH 7.5, 2 mM EDTA, 1 mM DTT, 200 mM NaCl. The GST-tagged proteins were then eluted by 10 applications (1 mL each) of 25 mM Tris-HCl, pH 7.5, 10 mM reduced-glutathione, 100 mM NaCl, 1 mM DTT, 10% glycerol and stored at −70° C.

The protein kinase activities of the various Kit mutants 200-500 ng were assayed in the presence or absence of inhibitors, 20 mM Tris-HCl, pH 7.6, 3 mM MnCl$_2$, 3 mM MgCl$_2$, 1 mM DTT, 10 μM Na$_3$VO$_4$, 3 μg/mL poly(Glu, Tyr) 4:1, 1% DMSO, 1.5 μM ATP (γ-[$^{33}$P]-ATP 0.1 μCi). The assay (30 μL) was carried out in 96-well plates at ambient temperature for 30 minutes and the reaction terminated by the addition of 20 μL of 125 mM EDTA. Subsequently, 30 μl of the reaction mixture were transferred onto Immobilon-PVDF membrane (Millipore, Bedford, Mass., USA) previously soaked for 5 minutes with methanol, rinsed with water, then soaked for 5 minutes with 0.5% H$_3$PO$_4$ and mounted on vacuum manifold with disconnected vacuum source. After spotting all samples, vacuum was connected and each well rinsed with 200 μL 0.5% H$_3$PO$_4$. Membranes were removed and washed 4× on a shaker with 1.0% H$_3$PO$_4$, once with ethanol. Membranes were counted after drying at ambient temperature, mounting in Packard TopCount 96-well frame, and addition of 10 μL/well of Microscint (Packard). IC$_{50}$ values were calculated by linear regression analysis of the percentage inhibition of each compound in duplicate, at 4 concentrations (usually 0.01, 0.1, 1 and 10 μM). One unit of protein kinase activity is defined as 1 nmole of $^{33}$P transferred from [γ$^{33}$P]ATP to the substrate protein/minute/mg of protein at RT.

We claim:

1. A method of treating a KIT dependent disease in a patient, comprising administering to the patient an effective amount of a compound of formula

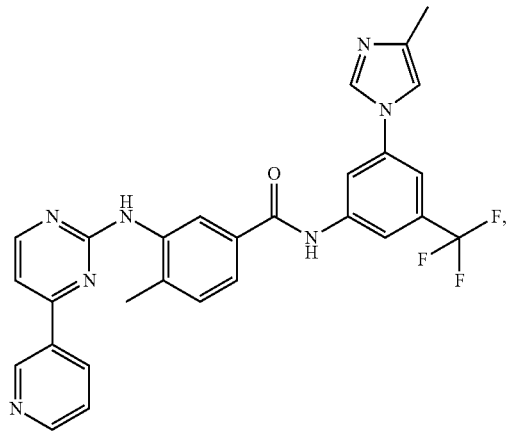

wherein the KIT dependent disease is systemic mastocytosis.

2. A method of claim 1, wherein the KIT dependent disease is resistant to treatment with imatinib.

* * * * *